United States Patent
Humphreys et al.

(10) Patent No.: US 9,535,266 B2
(45) Date of Patent: Jan. 3, 2017

(54) WAKE CIRCUIT FOR POWERED OPHTHALMIC LENS

(71) Applicant: Johnson & Johnson Vision Care, Inc., Jacksonville, FL (US)

(72) Inventors: Scott Robert Humphreys, Greensboro, NC (US); Robert Karl Schweickert, Monument, CO (US); Steven Phillip Hoggarth, Cary, NC (US); Seyed Ali Gorji Zadeh, Montreal (CA); Donald K. Whitney, Jr., West Melbourne, FL (US); Adam Toner, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 216 days.

(21) Appl. No.: 14/533,687

(22) Filed: Nov. 5, 2014

(65) Prior Publication Data
US 2016/0124248 A1 May 5, 2016

(51) Int. Cl.
| | |
|---|---|
| *H03L 7/00* | (2006.01) |
| *G02C 11/00* | (2006.01) |
| *G02C 7/04* | (2006.01) |
| *A61F 2/16* | (2006.01) |
| *H03K 19/0185* | (2006.01) |
| *G02C 7/08* | (2006.01) |
| *H02J 7/00* | (2006.01) |
| *H02J 9/00* | (2006.01) |
| *H03K 17/22* | (2006.01) |

(52) U.S. Cl.
CPC ............... *G02C 11/10* (2013.01); *A61F 2/16* (2013.01); *G02C 7/04* (2013.01); *G02C 7/083* (2013.01); *H02J 7/0031* (2013.01); *H02J 9/005* (2013.01); *H03K 17/22* (2013.01); *H03K 19/018507* (2013.01)

(58) Field of Classification Search
CPC ...................................................... G02C 11/10
See application file for complete search history.

(56) References Cited

U.S. PATENT DOCUMENTS

| | | | |
|---|---|---|---|
| 2008/0116945 A1 | 5/2008 | Sugio | |
| 2014/0148899 A1* | 5/2014 | Fehr | ..................... A61F 2/1624 623/6.22 |

FOREIGN PATENT DOCUMENTS

EP    2778751 A1    9/2014

OTHER PUBLICATIONS

European Search Report for corresponding EP Patent Application No. 15193014.6 dated Jan. 21, 2016.

* cited by examiner

*Primary Examiner* — Daniel Puentes
(74) *Attorney, Agent, or Firm* — Carl J. Evens

(57) ABSTRACT

A wake circuit is designed to minimize leakage current from a battery or other suitable energy source connected to various electronic components. The wake circuit essentially connects/disconnects or couples/decouples the battery or other power source from the other components when the device is in a storage state or otherwise idle.

24 Claims, 6 Drawing Sheets

Wake Circuit for Powered Ophthalmic Lens

WAKE CIRCUIT FOR POWERED OPHTHALMIC LENS

BACKGROUND OF THE INVENTION

1. Field of the Invention

The present invention relates to a wake circuit for a powered or electronic ophthalmic lens or other similar device, and more particularly, to a wake circuit that may be utilized to decouple/couple a battery or other energy source from other components of an electronic system to minimize leakage current drawn from the battery or other energy source.

2. Discussion of the Related Art

As electronic devices continue to be miniaturized, it is becoming increasingly more likely to create wearable or embeddable microelectronic devices for a variety of uses. Such uses may include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neurostimulators. A new, particularly useful field of application is in ophthalmic wearable lenses and contact lenses. For example, a wearable lens may incorporate a lens assembly having an electronically adjustable focus to augment or enhance performance of the eye. In another example, either with or without adjustable focus, a wearable contact lens may incorporate electronic sensors to detect concentrations of particular chemicals in the precorneal (tear) film. The use of embedded electronics in a lens assembly introduces a potential requirement for communication with the electronics, for a method of powering and/or re-energizing the electronics including power control or power management circuitry, for interconnecting the electronics, for internal and external sensing and/or monitoring, and for control of the electronics and the overall function of the lens.

The human eye has the ability to discern millions of colors, adjust easily to shifting light conditions, and transmit signals or information to the brain at a rate exceeding that of a high-speed internet connection. Lenses, such as contact lenses and intraocular lenses, currently are utilized to correct vision defects such as myopia (nearsightedness), hyperopia (farsightedness), presbyopia and astigmatism. However, properly designed lenses incorporating additional components may be utilized to enhance vision as well as to correct vision defects.

Contact lenses may be utilized to correct myopia, hyperopia, astigmatism as well as other visual acuity defects. Contact lenses may also be utilized to enhance the natural appearance of the wearer's eyes. Contact lenses or "contacts" are simply lenses placed on the anterior surface of the eye. Contact lenses are considered medical devices and may be worn to correct vision and/or for cosmetic or other therapeutic reasons. Contact lenses have been utilized commercially to improve vision since the 1950s. Early contact lenses were made or fabricated from hard materials, were relatively expensive and fragile. In addition, these early contact lenses were fabricated from materials that did not allow sufficient oxygen transmission through the contact lens to the conjunctiva and cornea which potentially could cause a number of adverse clinical effects. Although these contact lenses are still utilized, they are not suitable for all patients due to their poor initial comfort. Later developments in the field gave rise to soft contact lenses, based upon hydrogels, which are extremely popular and widely utilized today. Specifically, silicone hydrogel contact lenses that are available today combine the benefit of silicone, which has extremely high oxygen permeability, with the proven comfort and clinical performance of hydrogels. Essentially, these silicone hydrogel based contact lenses have higher oxygen permeability and are generally more comfortable to wear than the contact lenses made of the earlier hard materials.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered contract lenses may be designed to provide enhanced vision via zoom-in and zoom-out capabilities, or just simply modifying the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low-light conditions. The properly designed electronics and/or arrangement of electronics on lenses may allow for projecting an image onto the retina, for example, without a variable-focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This, coupled with a wireless data transmitter, could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The proper combination of devices could yield potentially unlimited functionality; however, there are a number of difficulties associated with the incorporation of extra components on a piece of optical-grade polymer. In general, it is difficult to manufacture such components directly on the lens for a number of reasons, as well as mounting and interconnecting planar devices on a non-planar surface. It is also difficult to manufacture to scale. The components to be placed on or in the lens need to be miniaturized and integrated onto just 1.5 square centimeters of a transparent polymer while protecting the components from the liquid environment on the eye. It is also difficult to make a contact lens comfortable and safe for the wearer with the added thickness of additional components.

Given the area and volume constraints of an ophthalmic device such as a contact lens, and the environment in which it is to be utilized, the physical realization of the device must overcome a number of problems, including mounting and interconnecting a number of electronic components on a non-planar surface, the bulk of which comprises optic plastic. Accordingly, there exists a need for providing a mechanically and electrically robust electronic contact lens.

As these are powered lenses, energy or more particularly current consumption, to run the electronics is a concern given battery technology on the scale for an ophthalmic lens. In addition to normal current consumption, powered devices or systems of this nature generally require standby current reserves, precise voltage control and switching capabilities to ensure operation over a potentially wide range of operating parameters, and burst consumption, for example, up to eighteen (18) hours on a single charge, after potentially remaining idle for years after initial manufacture and before first use. Accordingly, there exists a need for a system that is optimized for low-cost, long-term reliable service, safety and size while providing the required power.

In addition, because of the complexity of the functionality associated with a powered lens and the high level of interaction between all of the components comprising a powered lens, there is a need to coordinate and control the overall operation of the electronics and optics comprising a powered ophthalmic lens. Accordingly, there is a need for a system to control the operation of all of the other components that is safe, low-cost, and reliable, has a low rate of power consumption and is scalable for incorporation into an ophthalmic lens.

In order to optimize the size and/or volume of a battery or other power source for a powered lens, both the active current consumption of the device and the idle or standby current must be minimized. At the time of manufacture the device must be fully operational to allow testing of the device functionality and performance. Once the lens is assembled and tested it may remain on the shelf in a warehouse or a store for months or years before first use. The current consumption during this storage time must be minimized to allow as much of the battery capacity as possible to remain available when the device is first used by a wearer. The electronics that provide the desired functionality of the powered lens, such as complementary metal-oxide semiconductor (CMOS) devices, have leakage currents that are too high to be connected to the battery during the storage time. In addition, powered lenses may be similar to other contact lenses having an unbroken, smooth polymer surface around the internal components, with no direct mechanical or electrical contact available to the outside. Therefore there is a need for a powered lens having electronics that consume minimal current while in storage and may be placed into active operation without a direct mechanical or electrical contact to an external device. Further the device must be capable of being placed back into a low current storage state after assembly and testing.

SUMMARY OF THE INVENTION

The wake circuit for an electronic ophthalmic lens in accordance with the present invention overcomes the limitations associated with the prior art as briefly described above.

In accordance with one aspect, the present invention is directed to an electronic system including a wake circuit configured for use in at least one of on or in the body. The electronic system comprises functional electronics, including a digital controller and additional circuitry, a power supply for supplying power to the functional electronics, a wake logic circuit having a storage state and an active state configured to decouple the power supply from the functional electronics to minimize leakage current from the power supply when in the storage state, a switching element coupled to the power source, the wake logic circuit and the functional electronics, and a sensor coupled to the wake logic circuit, wherein the wake logic circuit is configured to switch from the storage state to the active state when the sensor is activated.

The present invention relates to a powered contact lens comprising an electronic system and/or electronics, which performs any number of functions, including actuating a variable-focus optic if included. The electronic system includes one or more batteries or other power sources, power management circuitry, one or more sensors, clock generation circuitry, control algorithms and circuitry, and lens driver circuitry as needed. In addition, the electronic system in accordance with the present invention further comprises a wake circuit that may be used to disconnect or decouple the battery or other energy source from portions of the electronic system, some of which is described above, to minimize leakage current drawn from the battery or other power supply/source during storage, thereby maximizing the storage and operating lifetime of the battery or other power source. Simply stated the wake circuit decouples the battery/power source from the remaining circuitry when power is not required and recouples it when power is required.

In one exemplary embodiment, the electronic system comprises a battery switch, which may be implemented in a number of ways as set forth herein, a photodiode or other suitable sensor, and a wake logic circuit having a storage state and an active state. In the active state the battery switch or switching element is closed, while in the storage state the battery switch or switching element is open. The wake circuit is configured to switch from the storage state to the active state when a bright light is shone on or directed onto the photodiode for a predetermined duration. If another type of sensor is utilized, other signals rather than bright light may be used. The wake circuit may be placed back into storage state by control circuitry in the electronic system in response to an external stimulus or a sensor response. The battery switch or switching element may be implemented in any number of suitable ways as described in detail herein.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
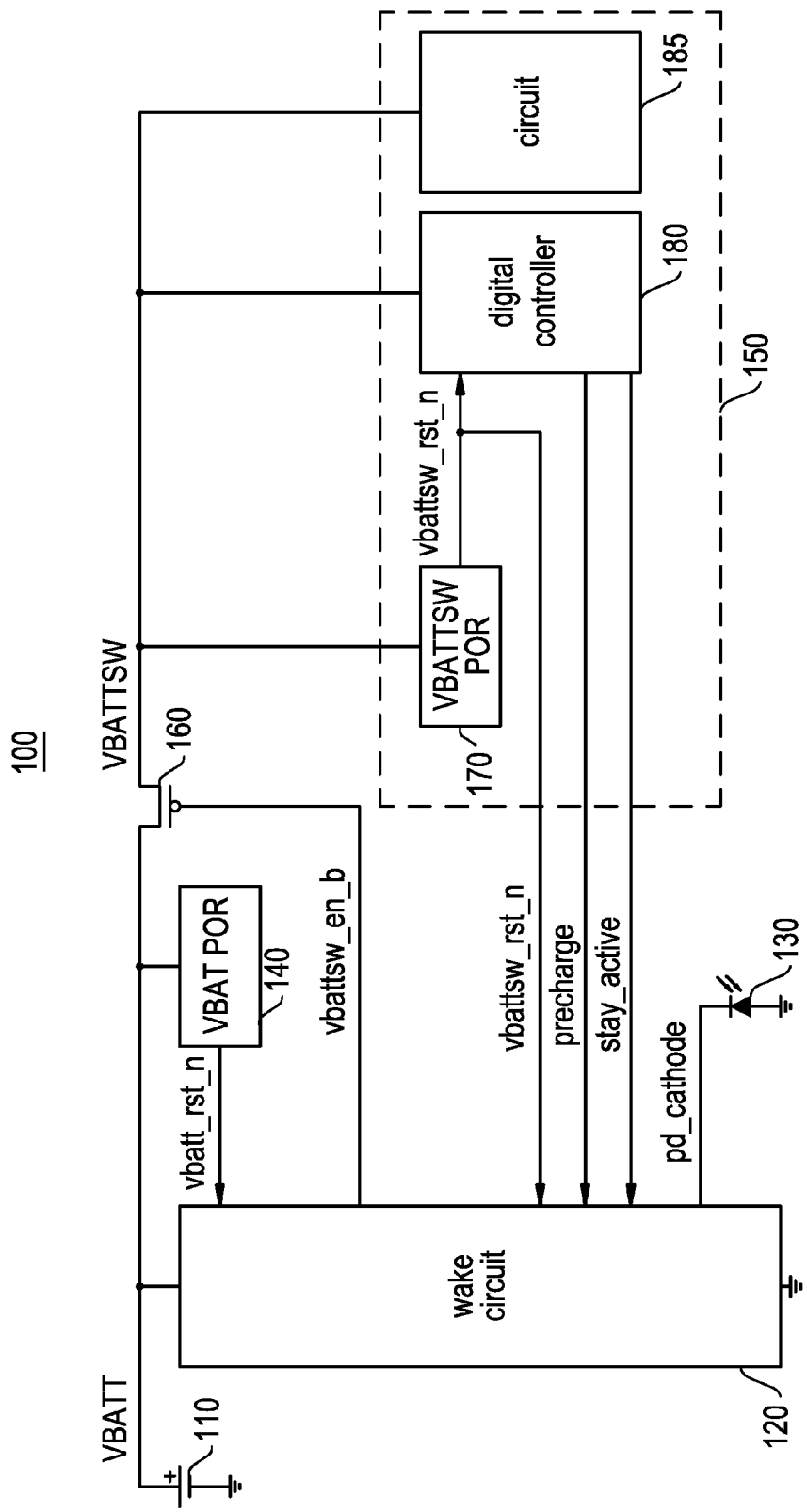
FIG. 1 illustrates a partial schematic and partial block diagram of a first exemplary embodiment of an electronic system in accordance with the present invention.

Conventional contact lenses are polymeric structures with specific shapes to correct various vision problems as briefly set forth above. To achieve enhanced functionality, various circuits and components may be integrated into these polymeric structures. For example, control circuits, microprocessors, communication devices, power supplies, power management circuitry, sensors, actuators, light-emitting diodes, and miniature antennas may be integrated into contact lenses via custom-built optoelectronic components to not only correct vision, but to enhance vision as well as provide additional functionality as is explained herein. Electronic and/or powered contact lenses may be designed to provide enhanced vision via zoom-in and zoom-out capabilities, or just simply modifying the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low light conditions. The properly designed electronics and/or arrangement of electronics on lenses may allow for projecting an image onto the retina, for example, without a variable focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This coupled with a wireless data transmitter could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

A powered or electronic contact lens in accordance with an exemplary embodiment of the present invention comprises the necessary elements to correct and/or enhance the vision of patients with one or more of the above described vision defects or otherwise perform a useful ophthalmic function. In addition, the electronic contact lens may be utilized simply to enhance normal vision or provide a wide variety of functionality as described above. The electronic contact lens may comprise a variable focus optic lens, an assembled front optic embedded into a contact lens or just simply embedding electronics without a lens for any suitable functionality. The electronic lens of the present invention may be incorporated into any number of contact lenses as described above. In addition, intraocular lenses may also incorporate the various components and functionality described herein. However, for ease of explanation, the disclosure will focus on an electronic contact lens to correct vision defects intended for single-use daily disposability.

Control of an electronic or a powered ophthalmic lens may be accomplished through a manually operated external device that communicates with the lens, such as a hand-held remote unit. For example, a fob may wirelessly communicate with the powered lens based upon manual input from the wearer. Alternately, control of the powered ophthalmic lens may be accomplished via feedback or control signals directly from the wearer. For example, sensors built into the lens may detect blinks and/or blink patterns. Based upon the pattern or sequence of blinks, the powered ophthalmic lens may change state, for example, its refractive power in order to either focus on a near object or a distant object.

The wake circuit of the present invention may be employed in a powered ophthalmic lens or powered contact lens comprising an electronic system, which actuates a variable-focus optic or any other device or devices configured to implement any number of numerous functions that may be performed. The electronic system includes one or more batteries or other power sources, power management circuitry, one or more sensors, clock generation circuitry, control algorithms and circuitry, and lens driver circuitry. The complexity of these components may vary depending on the required or desired functionality of the lens. The wake circuit of the present invention may also be utilized in any circuit or system requiring this type of functionality.

In accordance with the present invention, the electronic system further comprises a wake circuit that may be utilized to disconnect or decouple the battery or other energy storage device from at least a portion of the electronic system to minimize leakage current drawn from the battery during storage thereby maximizing the storage and operating lifetime of the battery. The wake circuit may also be configured to couple or reconnect the battery or other power supply or source to the rest of the electronic system as required. In some exemplary embodiments the electronic system comprises a battery switch or switching element, a photodiode or other sensor, and a wake logic circuit having a storage mode or state and an active mode or state. For ease of explanation and consistency, the specification shall only refer to storage state and active state rather than the use of the term mode. In the active state the battery switch is closed, while in the storage state the battery switch is open. The wake circuit is configured to switch from the storage state to the active state when a bright light is shone on or otherwise directed onto the photodiode for a predetermined duration. The light may be from a particular source or may simply be ambient light depending on how it is configured. The photodiode generates a photocurrent when light is shone on it. The wake circuit may be placed back into storage state by control circuitry in the electronic system in response to an external stimulus such as a wireless communication or a sensor response, after a predetermined delay time or other conditions as desired for the operation of the powered lens or other suitable device.

FIG. 1 illustrates, in block diagram form, an electronic system 100 in accordance with a first exemplary embodiment of the present invention. The electronic system 100 comprises a battery 110 coupled to a VBATT node for supplying power to the other components in the system, a wake logic circuit 120, a photodiode 130, a VBAT power-on reset (POR) circuit or generator 140, functional electronics 150, and a battery switch 160. Note that for clarity and ease of explanation not all grounds are shown in FIG. 1. The battery switch 160 as set forth in greater detail subsequently functions to electronically isolate the battery 110 from the functional electronics 150. As used herein, electronically isolate, decouple, disconnect and/or couple and connect shall all be construed to mean some type of direct or indirect connection or the severance thereof. Although a battery 110 is shown and described, it is important to note any suitable power source may be utilized. For example, various storage elements and/or inductive coils may be utilized, and it may be required that they be de-coupled from the remainder of the electronics for a particular reason. In addition, although a photodiode 130 is shown and described, any suitable sensor may be utilized. For example, the sensor may comprise an IR detector, a Hall-effect or reed sensor, a piezoelectric pressure sensor, an accelerometer or any other suitable electromechanical or electrochemical transducer. The photodiode 130 is connected to the wake logic circuit 120 via signal line/input pd_cathode. The battery switch 160 is configured to selectively couple/decouple the VBATT node to a switched battery node VBATTSW under control of the wake logic circuit 120.

As illustrated in FIG. 1, the battery switch 160 may comprise a P-type MOSFET that acts as a closed switch when the voltage at a gate terminal is below the VBATT node voltage coupled to a source terminal of the MOSFET by more than a device dependent threshold voltage. The wake logic circuit 120 is configured to provide an output signal vbattsw_en_b to control the voltage at the gate terminal of the battery switch 160 MOSFET. The functional electronics 150 provide desired operating functionality and features of the powered lens and provide indication signals to the wake logic circuit 120. The functional electronics 150 comprises a VBATTSW power-on reset (POR) circuit or generator 170, a digital controller 180 and a generic circuit 185 providing predetermined functionality. The VBATTSW POR circuit 170 is configured to provide a vbattsw_rst_n signal to the digital controller 180 and the wake circuit 120. The power-on reset circuits 140 and 170 are utilized to ensure that the circuits they are coupled to power-up in the correct initial state and are well known in the art. However, it is important to note that there is always a predetermined time or delay associated with power-on reset circuits as is explained subsequently. The VBAT POR circuit 140 is coupled to the VBATT node and is configured to provide an output vbatt_rst_n to the wake logic circuit 120 that is high when the voltage of the VBATT node is greater than a predetermined threshold for a predetermined time or delay and is low otherwise. A typical threshold value may be between 1.0 and 2.0 volts. The vbatt_rst_n signal thus may be used to provide an active-low reset signal to reset sequential logic elements such as latches and flip-flops operating from the battery supply as are commonly practiced in the art. The VBAT POR circuit 140 may be configured to provide a delay longer than the power-up or settling time of the wake logic circuit 120 to ensure that the output vbatt_rst_n is de-asserted after the wake logic circuit 120 is stabilized in a desired starting state. The VBATSW POR circuit 170 is coupled to the switched supply node VBATTSW and is configured to provide an output vbattsw_rst_n that is high when the voltage of the VBATTSW node is greater than a predetermined threshold for a predetermined time or delay and is low otherwise. A typical threshold value may be between 1.0 and 2.0 volts. The vbattsw_rst_n signal thus may be used to provide an active-low reset signal to reset sequential logic elements such as latches and flip-flops operating from the VBATTSW supply node, such as the digital controller 180. When reset, the digital controller 180 is configured to drive a precharge signal to a low value, and a stay_active signal to a high value for input into the wake logic circuit 120. The digital controller 180 may be configured to drive the precharge signal high or to drive the stay_active signal low in response to an external stimulus such as a wireless communication or a sensor response, after a predetermined delay time or other conditions as desired for the operation of the powered lens thereby placing the system into a STORAGE state.

The electronic system 100 is configured to draw minimal current from the battery 110 when in the STORAGE state by disconnecting/decoupling the functional electronics 150 from the battery 110. Further the wake logic circuit 120, the VBAT POR circuit 140 and the battery switch 160 are configured to draw minimal current under all conditions since they are always connected or coupled to the battery 110. These circuits may be configured to draw minimal current by techniques known in the art such as use of long gate lengths and minimum gate widths if implemented with Complementary Metal Oxide Semiconductor (CMOS) devices.

Figure 2:
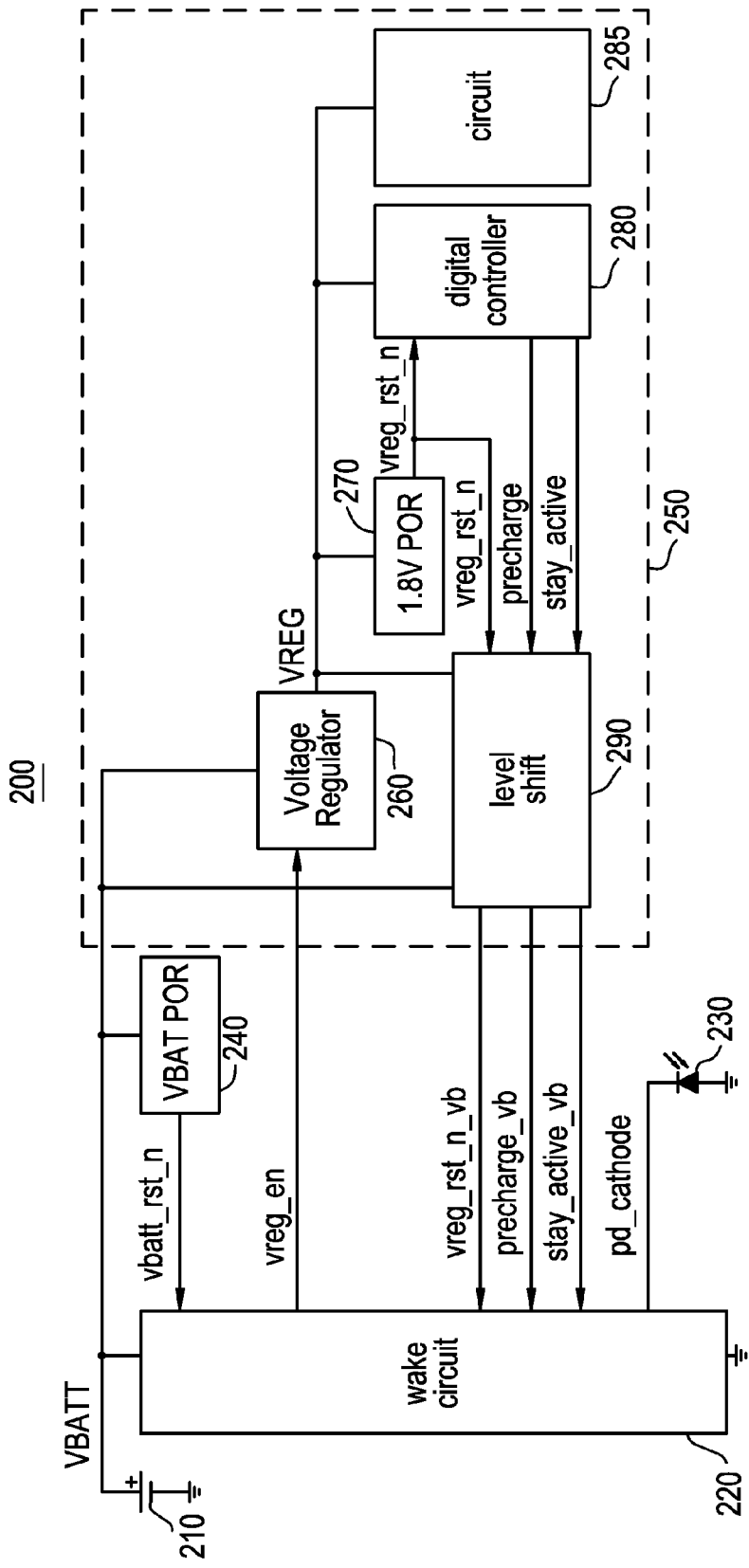
FIG. 2 illustrates a partial schematic and partial block diagram of a second exemplary embodiment of an electronic system in accordance with the present invention.

FIG. 2 illustrates, in block diagram form, a second exemplary embodiment of an electronic system 200 in accordance with the present invention. The electronic system 200 comprises a battery 210 coupled to a VBATT node for supplying power to the other components in the system, a wake logic circuit 220, a photodiode 230, a VBAT power-on reset (POR) circuit or generator 240, and functional electronics 250. The VBAT power-on reset (POR) circuit 240 operates in a manner similar to the VBAT power-on reset (POR) circuit 140 described above with respect to FIG. 1. The functional electronics 250 provide desired operating functionality and features of the powered lens and provide indication signals to the wake logic circuit 220. Once again, note that for clarity and ease of explanation not all grounds are shown in FIG. 2. The functional electronics 250 comprises a voltage regulator 260 configured to provide a regulated voltage on a node VREG, a VREG power-on reset (POR) circuit 270, a digital controller 280, a generic circuit 285 providing predetermined functionality and a level shifter 290 circuit. The VREG POR circuit 270 is coupled to the VREG node and is configured to provide an output vreg_rst_n that is high when the voltage of the VREG node is greater than a predetermined threshold for a predetermined time or delay and is low otherwise. A typical threshold value may be between 0.5 and 1.0 volts. The vreg_rst_n signal thus may be used to provide an active-low reset signal to reset sequential logic elements such as latches and flip-flops in the digital controller 280. When reset, the digital controller 280 is configured to drive a precharge signal to a low value and a stay_active signal to a high value. The digital controller 280 may be configured to drive the precharge signal high or to drive the stay_active signal low in response to external commands, a sensor reading, a time delay expiring or other conditions as desired for the operation of the powered lens.

The electronic system 200 is configured to draw minimal current from the battery 210 when in a STORAGE state by disconnecting/decoupling the functional electronics 250 from the battery 210. This is accomplished by disabling the voltage regulator 260. As is known in the art, the voltage regulator 260 may comprise a single transistor to couple the VBATT node to the VREG node when enabled and may be configured to regulate the base or gate voltage of the transistor to hold the VREG node voltage within a desired range when enabled and to shut off the transistor when disabled, thus decoupling the rest of the functional electronics 250 from the battery 210. The wake logic circuit 220 is configured to provide an output vreg_en to the voltage regulator 260 in order to enable or disable the voltage regulator 260 according to a state of the wake circuit 220. It will be appreciated that the voltage regulator 260 and the vreg_en signal functionally correspond to the battery switch 160 and the vbattsw_en_b signal of FIG. 1. Further the wake logic circuit 220, the VBAT POR circuit 240 and the voltage regulator 260 are configured to draw minimal current under all conditions since they are always connected to the battery 210. These circuits and the transistor in the voltage regulator 260 may be configured to draw minimal current by techniques known in the art, such as the use of long gate lengths and minimum gate widths if implemented with Complementary Metal Oxide Semiconductor (CMOS) devices. The level shifter 290 may be configured to translate the voltage level of the output signals of the VREG POR 270 circuit and the digital controller 280 to the VBATT voltage level in order to provide "rail to rail" or CMOS level signals to the wake logic circuit 220 as is commonly practiced in the art. For example, the level shifter 290 outputs vreg_rst_n_vb, precharge_vb and stay_active_vb, which correspond to level shifted versions of the VREG level signals vreg_rst_n, precharge and stay_active, respectively, to the wake logic circuit 220.

As set forth above with respect to FIGS. 1 and 2, various devices may be substituted for the battery and the photodetector as well as other circuits. For example, the voltage regulator 260 is substituted for the battery switch 160. Obviously, the switching functions provided by the voltage regulator 260 while providing the same or similar behavior and benefits as the battery switch 160, is implemented in a different manner. It is also important to note that various connections between the components in both FIGS. 1 and 2 have been omitted for ease of explanation similarly to the omission of various grounding connections as described above.

The digital controllers 180 and 280 and the circuits 185 and 285 described herein are part of the electronics utilized to not only correct vision, but to enhance vision as well as provide additional functionality as is described above.

Figure 3:
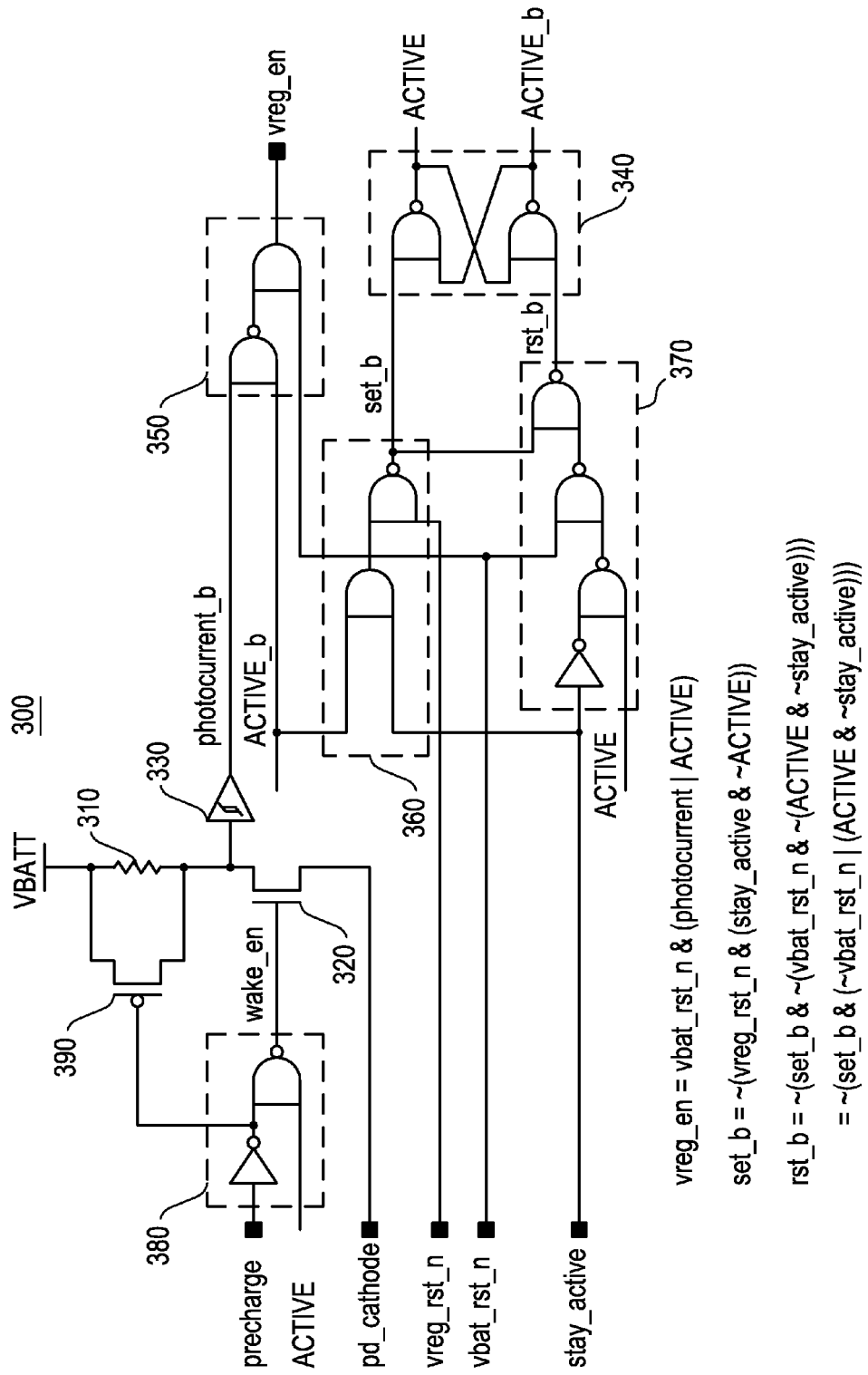
FIG. 3 illustrates an electronic schematic of an exemplary embodiment of a wake circuit in accordance with the present invention.

FIG. 3 illustrates a schematic representation of a wake logic circuit 300 in accordance with an exemplary embodiment of the present invention. The wake logic circuit 300 comprises a pull-up resistor 310, a photodiode switch 320, a Schmitt trigger 330, a latch 340, supply enable logic 350, set logic 360, reset logic 370, precharge logic 380 and a precharge switch 390. The wake logic circuit 300 also has logic inputs precharge, vreg_rst_n, vbat_rst_n and stay_active, a logic output vreg_en and a photodiode connection terminal pd_cathode. The state of the latch 340 corresponds to a state of the electronic system. When the latch 340 is set the system is in an ACTIVE state. When the latch 340 is not set the system may be in a STORAGE state or an intermediate state. The latch 340 has an ACTIVE output having an active high value when the latch is set, and the ACTIVE output value is low when the latch is not set. The latch 340 also has an ACTIVE_b output having a value equal to the inverse of the ACTIVE output. Note that the suffix_b used in signal names and logic statements is used herein to indicate an inverted version of the signal name without the suffix, as is commonly practiced in the relevant art. The latch 340 has a set_b logic input and a rst_b logic input configured respectively either to set the latch or reset (or clear) the latch when low. A first terminal of the pull-up resistor 310 is coupled to a VBATT node corresponding to the positive terminal of a battery such as shown in FIG. 1 and FIG. 2, and a second terminal of the pull-up resistor 310 is coupled to a first terminal of the photodiode switch 320 and an input of the Schmitt trigger 330. An output of the Schmitt trigger 330 is coupled to a node photocurrent_b. The Schmitt trigger 330 is configured to drive its output at either a high or a low voltage when the voltage at its input falls above a predetermined high threshold or below a predetermined low threshold, respectively, as is commonly practiced in the art. A second terminal of the photodiode switch 320 is coupled to a cathode terminal of a photodiode through a terminal labeled pd_cathode, and as shown in FIG. 1 and FIG. 2. The pull-up resistor 310 acts or functions to hold the voltage at the second terminal of the pull-up resistor 310 at or close to the VBATT node voltage when little current is drawn through the photodiode switch 320. When the photodiode switch 320 is closed and precharge switch 390 is open, current drawn by a photodiode coupled to the pd_cathode terminal pulls the voltage at the second terminal of the resistor 310 down away from the VBATT voltage toward ground. This causes the output of the Schmitt trigger 330 to drive the photocurrent_b node to a low voltage thus indicating that current is present in the photodiode. A light intensity threshold or a photocurrent threshold is determined by the responsivity of the photodiode, the value of the pull-up resistor 310 and the low threshold of the Schmitt trigger 330. Similarly, if another sensor is utilized instead of or in place of a photodiode, the corresponding threshold would be determined by that particular sensor, the value of the pull-up resistor 310, and the low threshold of the Schmitt trigger 330.

The light intensity threshold may be made adjustable for several reasons. A product may implement an opaque storage package, a device containing a wake circuit contained within the package, and a removable cover to gain access to the device. In this example, the wake circuit may be configured with a threshold to activate upon removal of the cover and subsequent exposure to ambient light typical in a bathroom, for example 100 to 500 lux. An alternate product configuration may require a higher light level, for example 1000 lux, to surpass the wake threshold. A higher wake threshold may be useful for one or more of reducing current consumption in the STORAGE mode, preventing wakeup during manufacturing, or to ensure the electronic system remains in the STORAGE mode until a deliberate exposure to bright light. Accordingly, the value of the pull-up resistor 310 and the low threshold of the Schmitt trigger may be made adjustable through hardware or software modifications, for example, via an electronic trim or fuse operation as is commonly used in semiconductor manufacturing, via communication from an external device to the digital controller 180 or 280, or during manufacture of the components or circuits comprising the electronic system. Programming or software changes to the light intensity threshold would be stored in a non-volatile memory such as electronic fuse, EEPROM, FLASH memory or other suitable memory types to maintain the modified values after the electronic system is placed back in to STORAGE mode.

The logic circuits 350, 360, 370 and 380 are configured to implement the following functions. The supply enable logic 350 is configured to drive vreg_en output high when vbat_rst_n is high and either photocurrent is present or the latch 340 is in the active state; the vreg_en output is low otherwise. Thus the vreg_en output may be used to close a battery switch or enable a voltage regulator when the battery voltage is high and either photocurrent is present or the latch 340 is in the ACTIVE state. The set logic 360 is configured to drive the set_b signal low to set the latch 340 when the vreg_rst_n signal is high and the stay_active signal is high and the latch 340 is not in the ACTIVE state; the set_b signal is high otherwise. The reset logic 370 is configured to drive the rst_b signal low to reset (or clear) the latch 340 when the set_b signal is inactive (high) and either the vbat_rst_n signal is low indicating the electronic system is being initially connected to a battery or when the latch 340 is in the ACTIVE state and the stay_active signal is low. The precharge logic 380 is coupled to the precharge switch 390 and to the photodiode switch 320. The precharge logic 380 is configured to close the precharge switch 390 when the precharge input signal is high. The precharge logic 380 is also configured to close the photodiode switch 320 via a wake en signal when the precharge input signal is high or when the latch 340 is not in the ACTIVE state. The precharge switch 390 and the photodiode switch 320 are open when these conditions are not met.

FIG. 3 illustrates a possible implementation of the logic circuits 350, 360, 370 and 380 and the latch 340 using Boolean logic gate signals as are commonly used in the art. It will be appreciated by those of ordinary skill in the art that the set logic 360 and reset logic 370 are configured to prevent driving both the set and reset signals set_b and rst_b to active (low) values simultaneously which can corrupt the simple cross coupled latch illustrated. It will be appreciated that the photodiode switch 320 minimizes current drawn from VBATT by the photodiode when in the ACTIVE state and that the photodiode may be used for other purposes when in the ACTIVE state. It should also be appreciated that the wake logic circuit 300 may be utilized with other types of sensors configured to or conditioned with the appropriate interfacing circuitry to sink a current in response to a stimulus condition.

Figure 4:
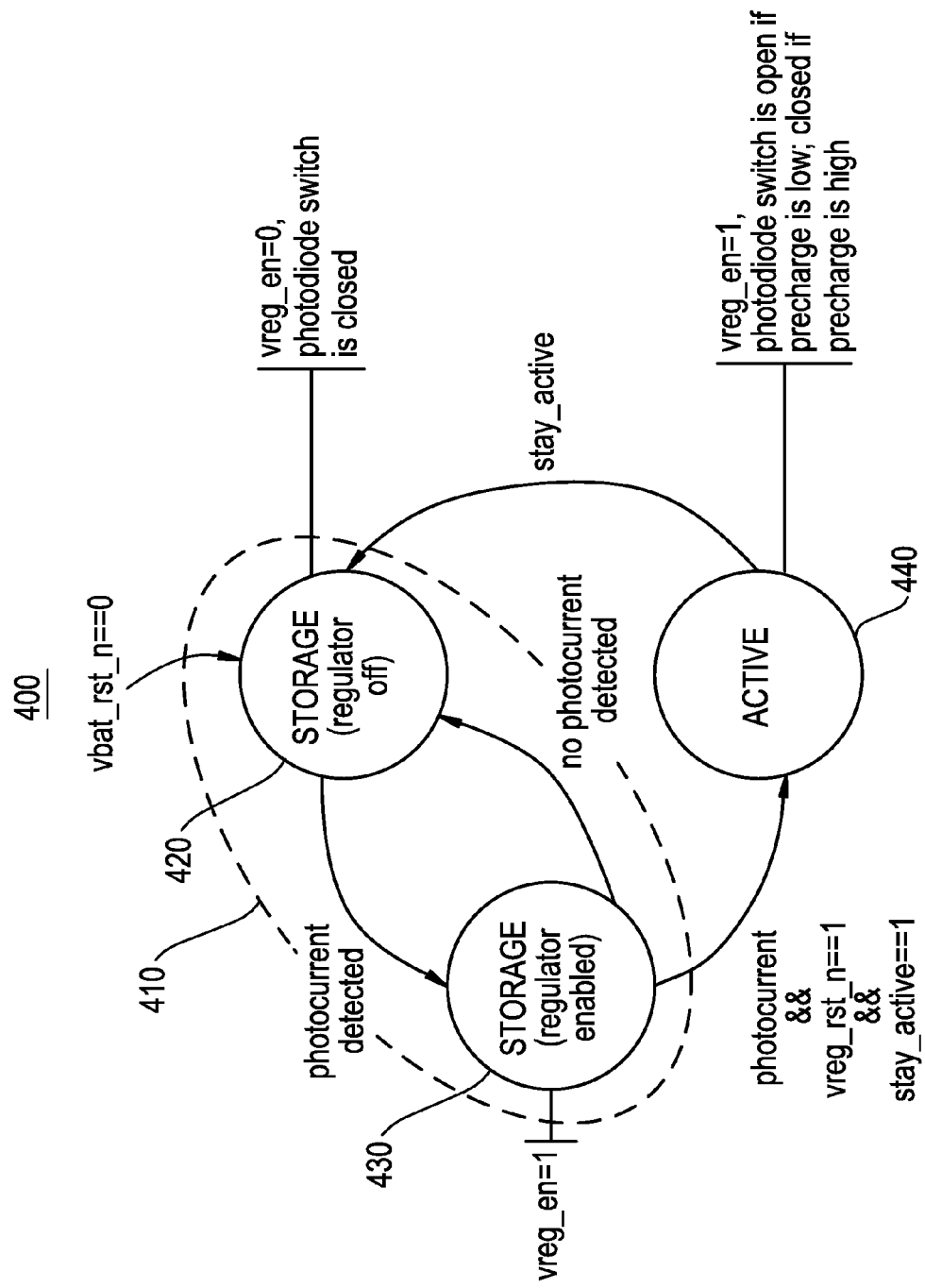
FIG. 4 illustrates an exemplary state transition diagram of a wake circuit in accordance with the present invention.

FIG. 4 illustrates a state flow diagram 400 in accordance with an exemplary embodiment of the present invention and generally corresponding to the wake logic circuit 300. The states illustrated correspond to the possible states of the system, as may correspond to the state of the latch 340. The system has two primary states, a STORAGE state 410 and an ACTIVE state 440. The STORAGE state 410 may be thought of as comprising two sub-states STORAGE (regulator off) 420 and STORAGE (regulator enabled) 430. When the system is first powered on by connecting a battery or other power source, the system enters the STORAGE (regulator off) state 420. A VBATT POR such as the VBATT POR 140 or VBATT POR 240 may provide reset signal vbatt_rst_n to reset the latch 340. In the STORAGE (regulator off) state 420 the vreg_en output is driven low and the photodiode switch 320 is closed. The system moves from the STORAGE (regulator off) state 420 to the STORAGE (regulator enabled) state 430 when photocurrent is detected. In the STORAGE (regulator enabled) state 430 the vreg_en output is driven high, thus closing a battery switch or enabling a voltage regulator. The system moves to the ACTIVE state 440 when photocurrent is detected, the stay_active signal is high and the vreg_rst_n signal is low. These conditions correspond to photocurrent being present in the photodiode, the digital controller 180 or 280 requesting to move to the ACTIVE state and the VBATTSW POR 170 or VREG POR 270 indicating that the supply voltage to the digital controller 180 or 280 is sufficiently high to have a valid signal value on the stay_active signal. If the photocurrent is no longer detected before the vreg_rst_n signal goes high the system returns to the STORAGE (regulator off) state 420. In the ACTIVE state the vreg_en signal is driven to a high value, and the wake logic circuit 300 controls the photodiode switch 320 to be open and the precharge switch 390 to be open or closed if the precharge signal is low or high, respectively. The system returns to the STORAGE (regulator off) state 420 when the stay_active signal is set to a low value.

Figure 5:
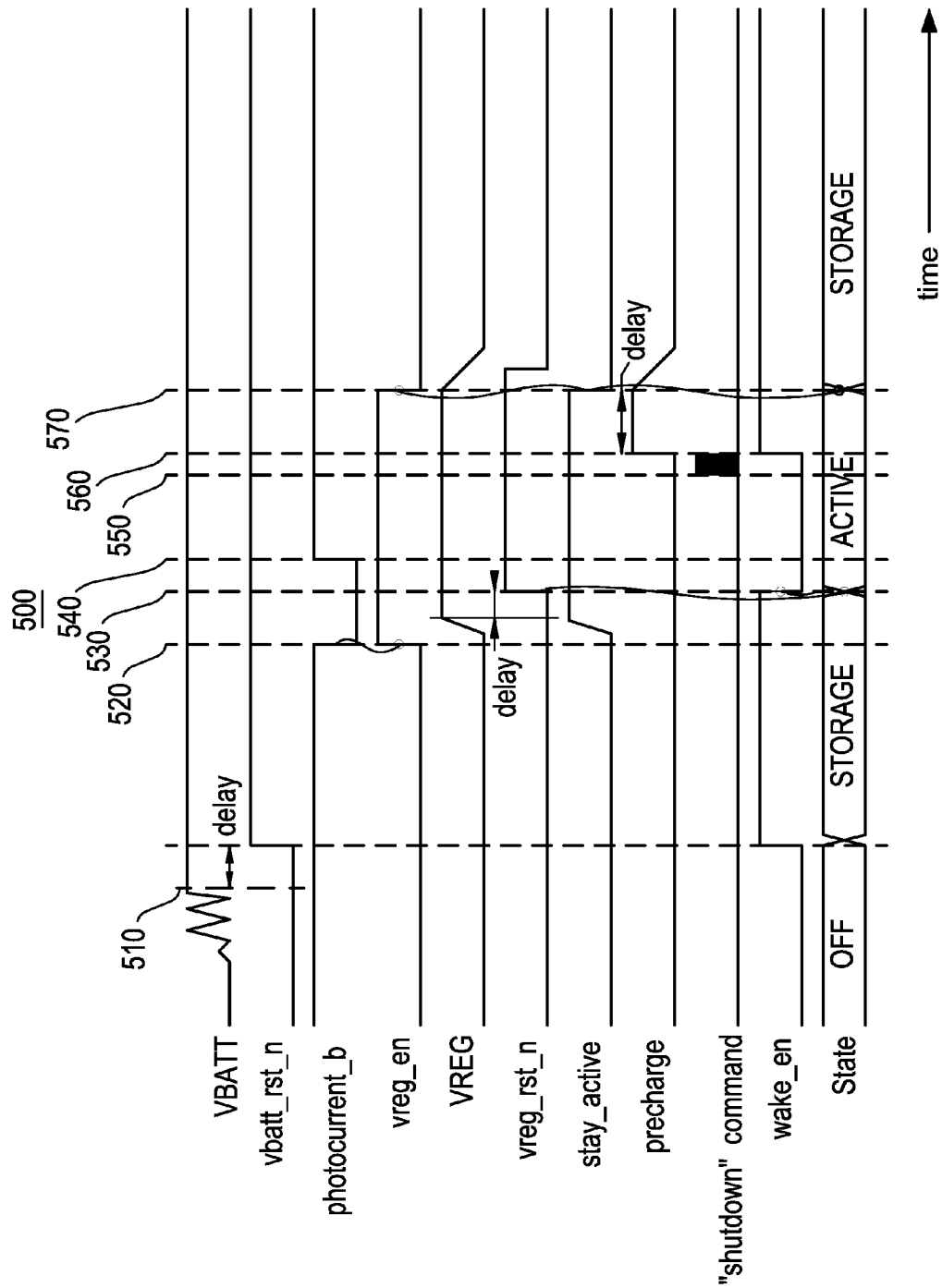
FIG. 5 illustrates an exemplary timing diagram of a powered lens comprising a wake circuit in accordance with the present invention.

FIG. 5 illustrates a timing diagram 500 in accordance with an exemplary embodiment of the present invention and generally corresponding to the electronic system 200, the wake logic circuit 300 and the state diagram 400.

Prior to time 510 and after a battery or other power source has been coupled to the VBAT node, the VBATT POR 240 initially drives a low level on (or asserts) the vbatt_rst_n signal. Following a short delay after time 510, the VBATT POR 240 drives a high level on (or de-asserts) the vbatt_rst_n signal and the wake en signal is driven high. After the VBATT POR 240 has de-asserted the vbatt_rst_n reset signal, the latch 340 and the electronic system 200 are in the STORAGE state 410 and in particular the STORAGE (regulator off) state 420.

At time 520 light is shone on the photodiode 230, photocurrent pulls the second terminal of the pull-up resistor 310 down and the photocurrent_b node is driven low by the Schmitt trigger 330. The vreg_en logic 350 drives the vreg_en signal high enabling the voltage regulator 260. This corresponds to the STORAGE (regulator enabled) state 430.

At time 530 the VREG POR 270 drives the vreg_rst_n signal high after a short delay indicating that the VREG voltage is above the threshold of the VREG POR 270 and the digital controller 280 drives the stay_active signal high. The electronic system 200 moves to the ACTIVE state 440 at this time 530 because the three necessary conditions are met: photocurrent is present, the vreg_rst_n signal is high and the stay_active signal is high. It will be appreciated that by requiring the presence of these three conditions to move to the ACTIVE state 440 the electronic system 200 is not triggered by short duration light pulses on the photodiode 230 and that the ACTIVE state 440 is not entered until the VREG supply voltage has stabilized. The wake en signal is driven low when the ACTIVE state is entered at a time 530 (i.e. the ACTIVE signal is driven high).

Also in the ACTIVE state 440 the photodiode switch 320 is open and the photocurrent_b signal returns to the high value, pulled up by resistor 310.

At time 540 the light is no longer shining on the photodiode 230. The electronic system 200 and latch 340 remain in the ACTIVE state 440.

At time 550 the digital controller 280 receives a "shutdown" command, which may correspond to one or more predetermined conditions such as in response to external commands, a sensor reading, a time delay expiring or other conditions as desired for the operation of the powered lens and drives the precharge signal high at time 560. At time 560, the wake en signal is also driven high in response to the precharge signal being driven high. In response, the precharge logic 380 closes the precharge switch 390 while maintaining the photodiode switch 320 open, thus precharging the cathode (and the associated capacitance) of the photodiode 230 to the VBATT voltage. After a time delay the digital controller 280 drives the stay_active signal low (or "de-asserts" the stay_active signal) at time 570. This causes the reset logic 370 to reset (or clear) the latch 340 which then drives the ACTIVE signal low and returns the electronic system 200 to the STORAGE state 410. In response, the supply enable logic 350 drives the vreg_en signal low, shutting down the voltage regulator 260. The time delay provided by the digital controller 280 allows use of the photodiode 230 for infrared or visible light communications, for example, and ensures the associated photocurrent is no longer present when de-asserting the stay_active signal thus avoiding false re-entry to the ACTIVE state 440 immediately after entering the STORAGE state 410. The time delay may be provided by a state machine transition after one or more cycles of delay, an RC delay circuit or other suitable means that are known in the art.

Therefore the present invention provides for a powered lens having electronics that consume minimal current while in storage and may be placed into active operation without a direct mechanical or electrical contact to an external device. Further the present invention allows the device to be placed back into a low current storage state after assembly and testing.

As set forth above, the wake circuit of the present invention may be utilized in a powered ophthalmic device such as a contact lens comprising a number of components. The proper combination of components could yield potentially unlimited functionality; however, there are a number of difficulties associated with the incorporation of extra components on a piece of optical-grade polymer that makes up the contact lens. In general, it is difficult to manufacture such components directly on the lens for a number of reasons, as well as mounting and interconnecting planar devices on a non-planar surface. It is also difficult to manufacture to scale and form. The components to be placed on or in the lens need to be miniaturized and integrated onto just 1.5 square centimeters of a transparent polymer, or more particularly, seventeen (17) square millimeters, while protecting the components from the liquid environment on the eye. It is also difficult to make a contact lens comfortable and safe for the wearer with the added thickness of additional components.

In addition to the size requirements set forth herein, electronic devices incorporated into a contact lens have to be robust and safe for use in an essentially aqueous environment. Tears have a pH of about 7.4 and are about 98.2 percent water and 1.8 percent solids, including electrolytes such as sodium, potassium, calcium, magnesium, and chlorides. This is a somewhat harsh environment in which to introduce electronics. Also, contact lenses are generally designed to be worn for at least four hours and preferably longer than eight hours. Electronic components require energy. This energy may be supplied from any number of sources, including built-in batteries. Since batteries and other potential energy sources have limited potential at these sizes, the wake circuit of the present invention is utilized. In addition, all electronic components are preferably designed to consume as little power as possible so that the contact lenses may be worn for a given period of time even after sitting idle for a given period of time (shelf life). Finally, all components in an electronic contact lens have to be biocompatible and safe. Accordingly, all electronics incorporated into the contact lens have to meet all of the above design parameters; namely, size, survivability in an aqueous solution, power consumption and safety.

In one exemplary embodiment, the electronics and electronic interconnections are made in a peripheral zone of a contact lens rather than in an optic zone of the lens. Typically, a contact lens has an optic zone with one or more powers for vision correction and/or enhancement and a peripheral zone surrounding the optic zone to provide the lens with mechanical stability. In accordance with an alternate exemplary embodiment, it is important to note that the positioning of the electronics need not be limited to the peripheral zone of the contact lens. All of the electronic components described herein may be fabricated utilizing thin-film technology and/or transparent materials. If these technologies are utilized, the electronic components may be placed in any suitable location as long as they are compatible with the optics.

It is important to note that the circuitry described herein may be implemented in hardware, software or a combination of hardware and software. In addition, the circuit board utilized herein may comprise any suitable substrate, including copper traces on a flexible polyimide substrate with a nickel-gold surface finish.

Figure 6:
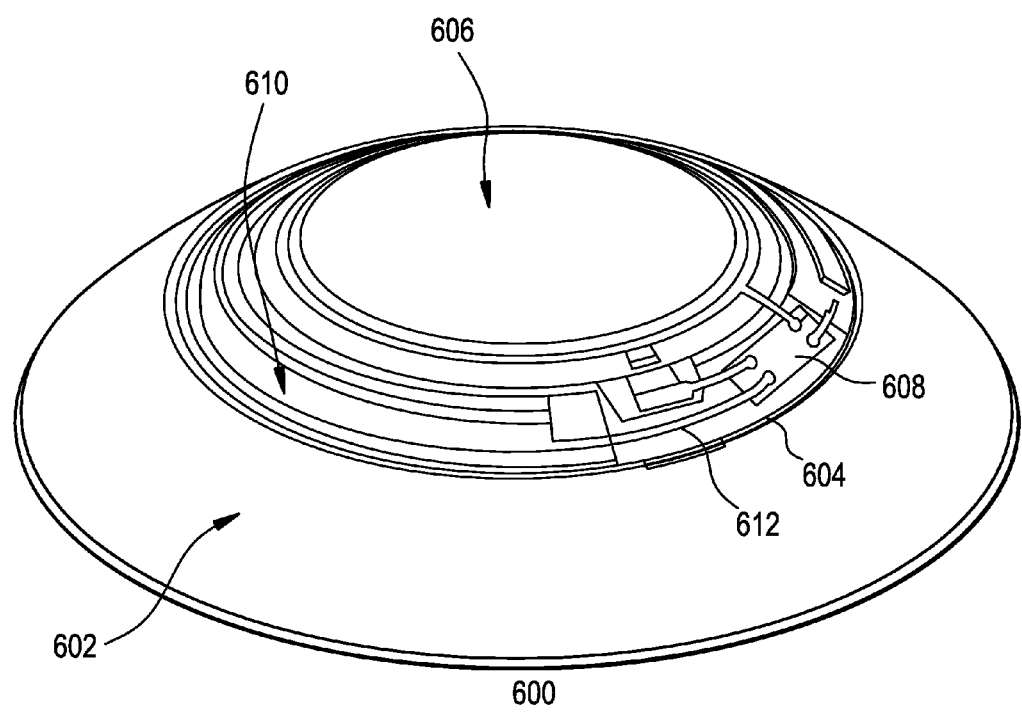
FIG. 6 is a diagrammatic representation of an exemplary electronic insert, including a wake circuit, for a powered contact lens in accordance with the present invention.

Referring now to FIG. 6, there is illustrated an exemplary contact lens with an electronic insert in accordance with one exemplary embodiment of the present invention. The exemplary contact lens 600 comprises a soft plastic portion 602 which comprises an electronic insert 604. This electronic insert 604 includes a lens 606 which is activated or controlled by the electronics described herein, for example, focusing near or far depending up activation. Circuitry 608 mounts onto the insert 604 and is connected to a power source 610, such as batteries via one or more electrical interconnect traces 612. Additional circuitry may also be connected via the electrical interconnect traces 612. Circuitry 608 may include any of the components set forth herein, including the wake circuit.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An electronic system including a wake circuit configured for use in at least one of on or in the body, the electronic system comprising:
   functional electronics, including a digital controller and additional circuitry;
   a power supply for supplying power to the functional electronics;
   a wake logic circuit having a storage state and an active state configured to decouple the power supply from the functional electronics to minimize leakage current from the power supply when in the storage state;
   a switching element coupled to the power source, the wake logic circuit and the functional electronics;
   a first power-on reset circuit coupled between the power supply and the wake logic circuit and configured to ensure a proper initial state for the wake logic circuit on power-up and hold the wake circuit in a reset condition for at least as long as a power-up stabilization time of the wake logic circuit;
   a second power-on reset circuit coupled between the switching element and the functional electronics and configured to ensure a proper initial state for the functional electronics on power-up; and
   a sensor coupled to the wake logic circuit, the sensor comprising a photodetector and wherein the wake logic circuit is configured to switch from the storage state to the active state when at least one of the sensor is activated in response to light having an intensity greater than a predetermined threshold being shone on the photodetector or in response to an output of the second power-on reset circuit.

2. The electronic system including a wake circuit according to claim 1, wherein the power supply is a battery.

3. The electronic system including a wake circuit according to claim 1, wherein the switching element comprises a transistor.

4. The electronic system including a wake circuit according to claim 1, wherein the switching element comprises a voltage regulator.

5. The electronic system including a wake circuit according to claim 1, wherein the photodetector comprises a photodiode.

6. The electronic system including a wake circuit according to claim 1, wherein the system is incorporated into an ophthalmic device.

7. The electronic system including a wake circuit according to claim 6, wherein the ophthalmic device comprises a contact lens.

8. The electronic system including a wake circuit according to claim 6, wherein the ophthalmic device comprises an intraocular lens.

9. The electronic system including a wake circuit according to claim 1, wherein a portion of the functional electronics, the wake logic circuit, the switching element and sensor are implemented in an integrated circuit.

10. The electronic system including a wake circuit according to claim 9, wherein the integrated circuit is at least one of incorporated onto or incorporated into a circuit board.

11. The electronic system including a wake circuit according to claim 10, wherein the circuit board is configured as an annular ring and formed into a conical section for incorporation into a contact lens.

12. The electronic system including a wake circuit according to claim 10, wherein the circuit board is configured as an annular ring and formed into a conical section for incorporation into an intraocular lens.

13. The electronic system including a wake circuit according to claim 10, wherein the circuit board comprises at least one of a polymer or plastic insert with metalized traces.

14. The electronic system including a wake circuit according to claim 1, wherein the predetermined threshold is at least partially determined by a trim value adjustable during the manufacture of the electronic system.

15. The electronic system including a wake circuit according to claim 1, wherein the predetermined threshold is at least partially determined by a programmable value adjustable by communication with the electronic system.

16. The electronic system including a wake circuit according to claim 1, wherein the functional electronics further comprises a controller configured to place the wake logic circuit into the storage state.

17. The electronic system including a wake circuit according to claim 16, wherein the controller is further configured to place the wake logic circuit into the storage state in response to a sensor reading.

18. The electronic system including a wake circuit according to claim 16, wherein the controller is further configured to place the wake logic circuit into the storage state in response to a command received via a wireless communication.

19. The electronic system including a wake circuit according to claim 16, wherein the controller is further configured to place the wake logic circuit into the storage state after a predetermined time delay.

20. The electronic system including a wake circuit according to claim 1, wherein a portion of the functional electronics, the wake logic circuit, the switching element and sensor are implemented in two or more integrated circuits.

21. The electronic system including a wake circuit according to claim 20, wherein the two or more integrated circuits are at least one of incorporated onto or incorporated into a circuit board.

22. The electronic system including a wake circuit according to claim 21, wherein the circuit board is configured as an annular ring and formed into a conical section for incorporation into a contact lens.

23. The electronic system including a wake circuit according to claim 21, wherein the circuit board is configured as an annular ring and formed into a conical section for incorporation into an intraocular lens.

24. The electronic system including a wake circuit according to claim 21, wherein the circuit board comprises at least one of a polymer or plastic insert with metalized traces.

* * * * *